United States Patent
Sadabadi

(10) Patent No.: US 8,640,927 B2
(45) Date of Patent: Feb. 4, 2014

(54) DOSING-DEVICE

(76) Inventor: Mahbobeh Taghinejad Sadabadi, Oxie (SE)

( * ) Notice: Subject to any disclaimer, the term of this patent is extended or adjusted under 35 U.S.C. 154(b) by 0 days.

(21) Appl. No.: 13/449,656

(22) Filed: Apr. 18, 2012

(65) Prior Publication Data

US 2012/0211525 A1    Aug. 23, 2012

Related U.S. Application Data

(63) Continuation of application No. PCT/SE2010/000254, filed on Oct. 22, 2010.

Foreign Application Priority Data

Oct. 22, 2009 (SE) .................................. 0901365-7

(51) Int. Cl.
*B67D 3/00* (2006.01)

(52) U.S. Cl.
USPC ........................................ 222/187; 604/94.01

(58) Field of Classification Search
USPC ................ 222/187, 546, 189.06, 189.1, 190; 604/145–148, 94.01; 128/200.14, 128/200.21, 200.22
See application file for complete search history.

(56) References Cited

U.S. PATENT DOCUMENTS

| | | | | |
|---|---|---|---|---|
| 3,189,223 A | * | 6/1965 | Mackal | 222/1 |
| 3,655,102 A | * | 4/1972 | Moran | 222/484 |
| 4,200,229 A | * | 4/1980 | Spector | 239/57 |
| 4,932,567 A | * | 6/1990 | Tanabe et al. | 222/190 |
| 5,346,097 A | * | 9/1994 | Melland et al. | 222/132 |
| 5,921,236 A | * | 7/1999 | Ohki et al. | 128/203.15 |
| 7,017,573 B1 | * | 3/2006 | Rasor et al. | 128/200.24 |
| 7,909,264 B2 | * | 3/2011 | Dunne et al. | 239/44 |
| 2008/0067194 A1 | * | 3/2008 | Faurie | 222/189.07 |

FOREIGN PATENT DOCUMENTS

| | | | | |
|---|---|---|---|---|
| EP | 0495675 | | 7/1992 | |
| GB | 370058 | | 4/1932 | |
| JP | 2007-105365 | * | 4/2007 | 128/200.24 |
| WO | WO-92/21404 | * | 12/1992 | 128/200.24 |
| WO | 0001593 | | 1/2000 | |
| WO | 2009071713 | | 6/2009 | |

OTHER PUBLICATIONS

International Search Report from corresponding International Application No. PCT/SE2010/000254, dated Jun. 14, 2011.

* cited by examiner

*Primary Examiner* — Lien Ngo
(74) *Attorney, Agent, or Firm* — Renner, Otto, Boisselle & Sklar, LLP

(57) ABSTRACT

The invention relates to a measuring device with a container of the aromatic liquid. Dosing-device includes a spout for the release of aroma, and a pump to pump up the aromatic liquid from the container to a cushion, where the aroma from the cushion is delivered to the spout. In one embodiment the dosing-device comprises two spouts separated from each other by a distance proportioned to the nostrils and where the spouts stand out from the container for insertion into the nostrils. This design is particularly well suited to deliver aroma to the nose. The dosing-device is designed to interact with a lid with plugs arranged to seal the spouts. This way the aroma is kept concentrated until its lid is removed for dosing.

13 Claims, 2 Drawing Sheets

DOSING-DEVICE

RELATED APPLICATION DATA

This application is a continuation of International Application No. PCT/SE2010/000254, filed Oct. 22, 2010, which claims the benefit of Swedish Patent Application No. 0901365-7, filed Oct. 22, 2009, the disclosures of which are herein incorporated by reference in their entireties.

TECHNICAL FIELD

The present invention relates to a dosing-device according to the preamble of the independent claim.

It particularly refers to such a dosing-device designed to administer aroma.

BACKGROUND OF THE INVENTION

Aroma can be described with the concept to stimulate saliva production, which is especially important for people with reduced saliva production. Aroma can be added to such things like food or sprays, but to take up the aroma the food must be eaten by the user which is not always the optimal solution. The sprays aroma is spread freely in all directions and dosing method is therefore inefficient.

One purpose of the invention is to provide a measuring device capable of efficiently dispensing aromas.

These and other purposes are achieved by a dosing-device according to the characteristic elements of the independent claims.

SUMMARY OF THE INVENTION

The invention relates to a dosing-device including a container (1) for aromatic liquid. The dosing-device includes at least one spout (6a-b) to release the aroma, and a pump (2) to pump up the aromatic liquid from the container to a cushion (4), where the aroma from the cushion is delivered to at least one spout. This two-step process where the aromatic liquid is first pumped up to the pad and thereafter the aroma is released from the cushion. This is particularly effective, making the release of the aroma directed and keeps the aroma concentrated.

In a particular advantageous embodiment the dosage-device contains two spouts (6a-b) separated from each other by a distance proportional to the nostrils and where the spouts protrude from the container for insertion into the nostrils. This embodiment is particularly well-suited to efficiently deliver aroma to the nose.

The dosing-device is designed to interact with a lid (7) with plugs arranged to close the spouts. This way, the aroma is kept concentrated until its lid is removed for dosing.

DESCRIPTION OF A PREFERRED EMBODIMENT

Figure 1:
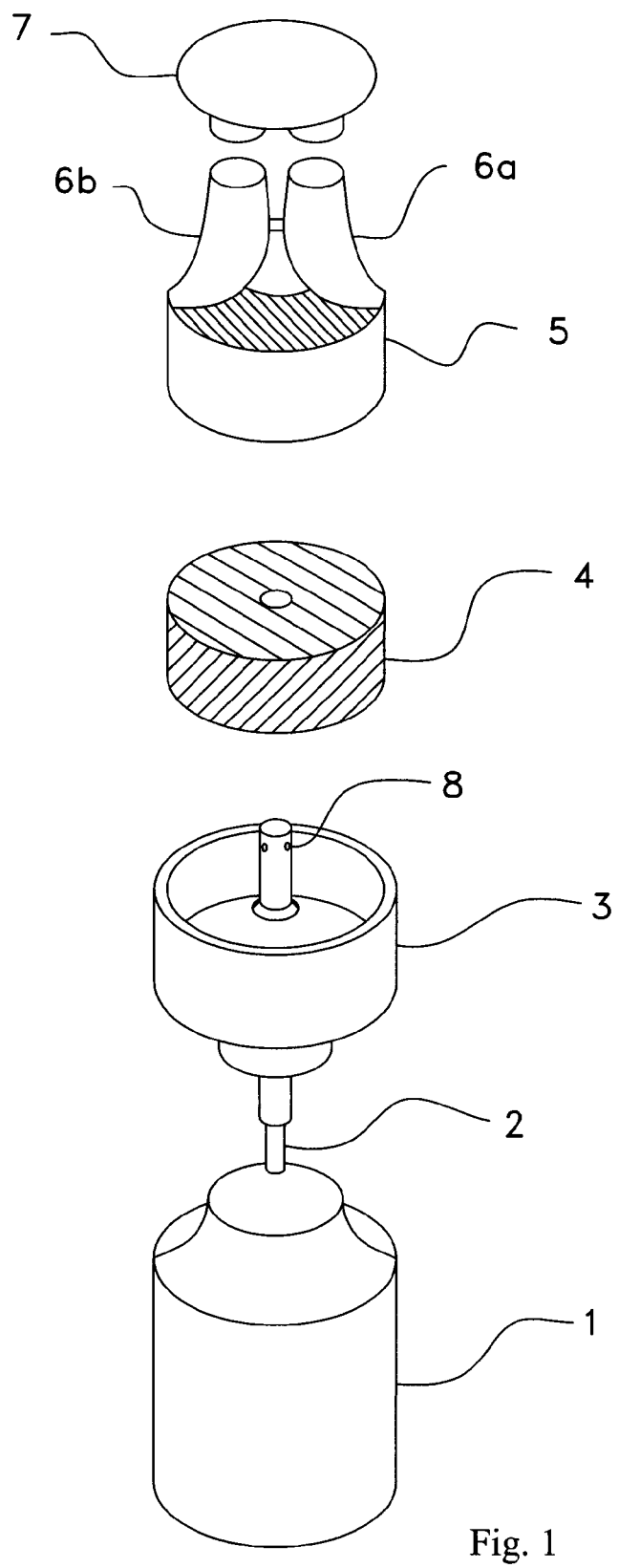
FIG. 1 shows an exploded view of the dosing-device

FIG. 1 shows an exploded view of the dosing-device in which all the components are illustrated separately. The dosing-device includes a container (1), a middle part (3), a cushion (4) and a top unit (5) with a lid (7). The middle part is mounted on top of the container, while the top part is held on top of the middle part. The middle part includes a pump (2) with a check valve, where the pump goes in the center of the cylindrical midsection. The pump goes a bit below the middle bottom part and reaches down into the container. By pressing the pump, the pump pumps out aroma from the reservoir up to the pump top and is pumped out through the openings (8) of the pump top.

The middle part is an open cup with a bottom and in this cup the pad (4) will be mounted. The pump goes through the middle parts base and reaches the middle parts center. The pad is cylindrical with a central hole that receives the pumps top. When the aroma is pumped from the container, it pumps out through the openings of the pumps top and received by the cushion. The cushion is made out of a liquid-absorbing material and stores recently pumped-up aromatic liquid. The fluid releases the aroma in the form of steam which is spread in the internal top unit.

The top section has a cylindrical lower-end which connects to the middle and upper part with two spouts (6a-b) with the openings facing up. The top section is hollow and encloses a volume of air with the aroma in gas-form. On the spouts openings are sealing-plugs in the lid arranged so that the aromatic air in the top part is kept contained until the lid is removed. The two plugs are placed on the lids flat top.

Figure 2:
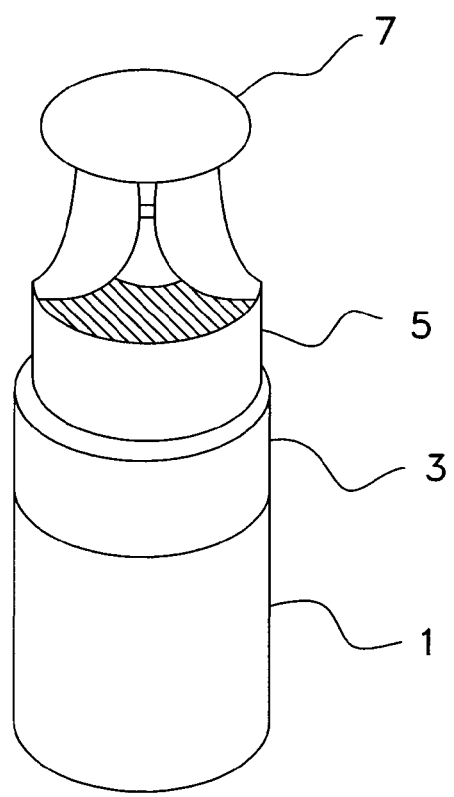
FIG. 2 shows the dosing-device assembled

FIG. 2 shows the dosing-device assembled. When in use the top part is pressed down so that the pump is pumping up the aromatic liquid from the container and ejecting it into the cushion. After this the cap is taken off and concentrated aroma is released through the tops two spouts.

The spouts are separated from each other with a distance that is proportional to the nostrils so that the aroma can be effectively dispensed. The spouts stick up a bit, so that they can be inserted in the nose to then further streamline the dosage. The aroma being dispensed can be lemon-based, but there are other aromas that are also effective to increase saliva production.

One particularly significant aspect of the use by the dosing-device is that it takes place in a two-step process. The two-step process includes a first step in which the aromatic liquid is pumped up to the pad and a second step where the aroma is then released to the pad. This two-step process is particularly effective because no liquid is directly sprayed as an aerosol. In addition, the shape of the spouts make the aroma-release directed and the pad then keeps the aroma further concentrated until it is dosed out.

The invention claimed is:

1. An aromatic gas dosing-device comprising:
   a container defining a first volume that retains an aromatic liquid;
   a middle part comprising a pump mechanism and defining a second volume;
   a liquid absorbing cushion disposed in the second volume, the pump mechanism pumps aromatic liquid from the container to the cushion; and
   a top unit, the middle part disposed between the container and the top unit, the top unit covering an upper surface of the cushion and comprising a spout for delivering the aromatic gas directly into a nostril of a user for treatment of reduced saliva production, the aromatic gas resulting from conversion of the aromatic liquid in the cushion to the aromatic gas; and
   wherein the pump mechanism comprises a stem and the cushion defines a hole through which the stem extends, the aromatic liquid pumped by the pump from the first volume to one or more openings at a top of the stem to eject the aromatic liquid adjacent the upper surface of the cushion.

2. A dosing-device according to claim 1, wherein the top unit comprises two spouts separated from each other by a distance proportional to the nostrils and where the spouts stand out from the container for insertion into the nostrils.

3. A dosing-device according to claim 1, further comprising a lid with plugs arranged to seal the spouts.

4. A dosing-device according to claim 1, further comprising a check valve in the pump mechanism.

5. A dosing-device according to claim 2, further comprising a lid with plugs arranged to seal the spouts.

6. A dosing-device according to claim 2, further comprising a check valve in the pump mechanism.

7. A dosing-device according to claim 3, further comprising a check valve in the pump mechanism.

8. A dosing-device according to claim 1, further comprising aromatic liquid stored in the first volume, the aromatic liquid formulated for stimulating saliva production in the user.

9. A dosing-device according to claim 1, wherein the dosing-device does not spray liquid to nostrils of the user.

10. A dosing-device according to claim 1, wherein the top unit defines an internal volume bound in part by the cushion and into which the aromatic liquid converts to the aromatic gas, the internal volume of the top unit storing and concentrating the aromatic gas until doing-out to the user.

11. An aromatic gas dosing-device comprising:
 a container defining a first volume that retains an aromatic liquid;
 a middle part comprising a pump mechanism and defining a second volume;
 a liquid absorbing cushion disposed in the second volume, the pump mechanism pumps aromatic liquid from the container to the cushion; and
 a top unit, the middle part disposed between the container and the top unit, the top unit covering an upper surface of the cushion and comprising a spout for delivering the aromatic gas directly into a nostril of a user for treatment of reduced saliva production, the aromatic gas resulting from conversion of the aromatic liquid in the cushion to the aromatic gas; and
 wherein the top unit defines an internal volume bound in part by the cushion and into which the aromatic liquid converts to the aromatic gas, the internal volume of the top unit storing and concentrating the aromatic gas until doing-out to the user.

12. A dosing-device according to claim 11, further comprising aromatic liquid stored in the first volume, the aromatic liquid formulated for stimulating saliva production in the user.

13. A dosing-device according to claim 11, wherein the dosing-device does not spray liquid to nostrils of the user.

* * * * *